(12) United States Patent
Domingue

(10) Patent No.: US 11,173,062 B1
(45) Date of Patent: Nov. 16, 2021

(54) MEDICAL SPLINT

(71) Applicant: Bradford R. Domingue, Lafayette, LA (US)

(72) Inventor: Bradford R. Domingue, Lafayette, LA (US)

( * ) Notice: Subject to any disclaimer, the term of this patent is extended or adjusted under 35 U.S.C. 154(b) by 0 days.

(21) Appl. No.: 16/602,090

(22) Filed: Aug. 5, 2019

Related U.S. Application Data

(63) Continuation-in-part of application No. 15/212,283, filed on Jul. 17, 2016, now abandoned.

(51) Int. Cl.
*A61F 5/00* (2006.01)
*A61F 5/058* (2006.01)

(52) U.S. Cl.
CPC ........ *A61F 5/05825* (2013.01); *A61F 5/0585* (2013.01); *A61F 5/05858* (2013.01)

(58) Field of Classification Search
CPC .. A61F 5/058; A61F 5/05825; A61F 5/05841; A61F 5/0585; A61F 5/05858; A61F 5/05866; A61F 5/01; A61F 5/0102
See application file for complete search history.

(56) References Cited

U.S. PATENT DOCUMENTS

| 4,209,011 A * | 6/1980 | Peck .................. A61F 5/05841 602/19 |
| 4,383,526 A * | 5/1983 | Robins ................. A61F 5/0585 602/15 |
| 8,622,944 B1 * | 1/2014 | Villahermosa ...... A61F 5/05825 602/5 |
| 9,226,841 B1 * | 1/2016 | Amodt ............... A61F 5/05841 |
| 9,717,622 B2 * | 8/2017 | McNally ............. A61F 5/05858 |
| 2008/0249445 A1 * | 10/2008 | Bailey ................ A61F 5/05841 602/6 |
| 2015/0119776 A1 * | 4/2015 | McNally ............. A61F 5/05858 602/12 |

FOREIGN PATENT DOCUMENTS

EP 0190543 A1 * 8/1986 ......... A61F 5/05825

* cited by examiner

*Primary Examiner* — Kim M Lewis
(74) *Attorney, Agent, or Firm* — Greg Mier

(57) ABSTRACT

A compact, lightweight, portable, foldable, multi-purpose, multi-functional, medical splint, primarily to use in emergency and/or remote situations to effectively provide quick, easy, and rigid immobilization to a person's limbs.

15 Claims, 15 Drawing Sheets

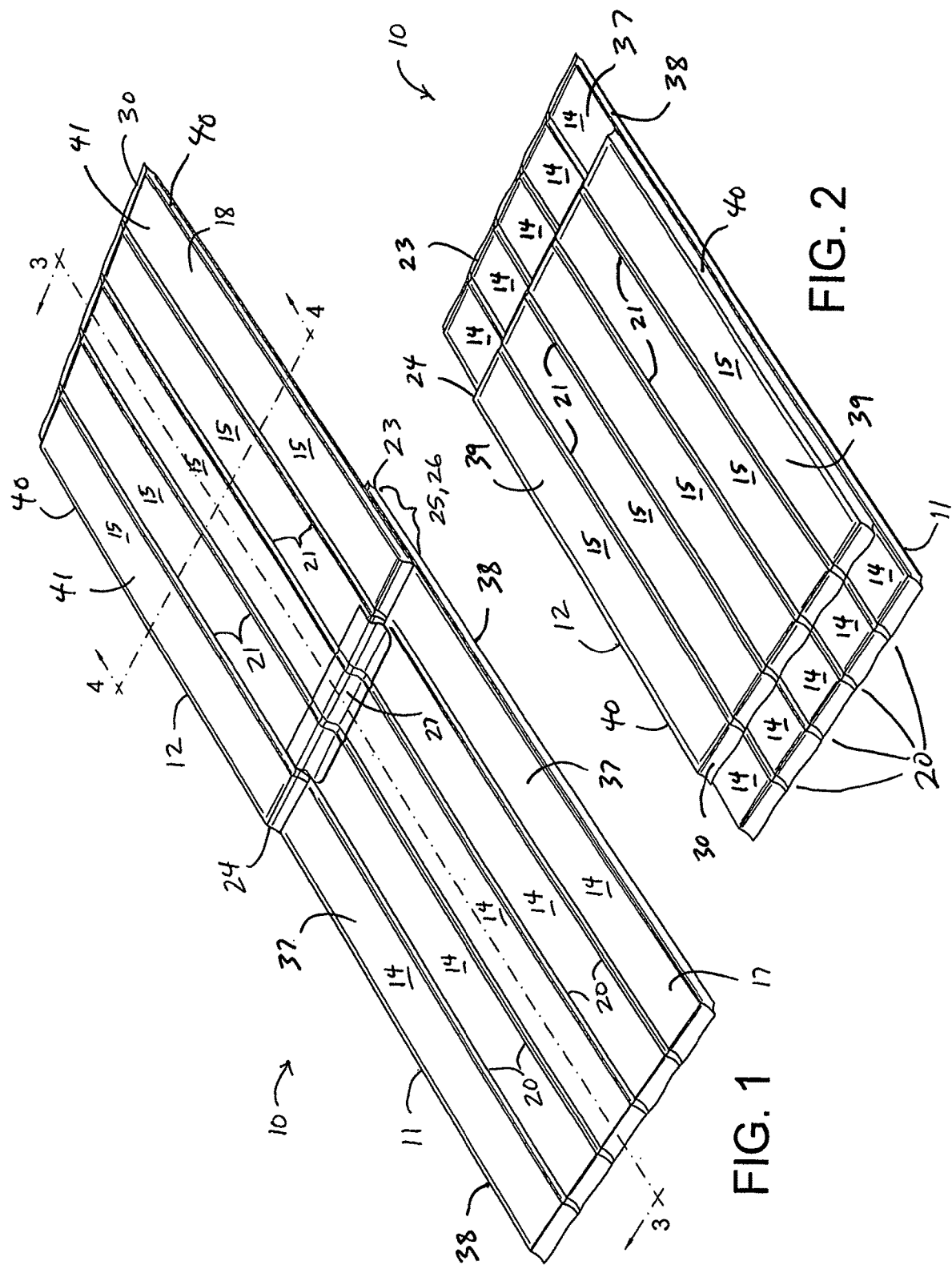

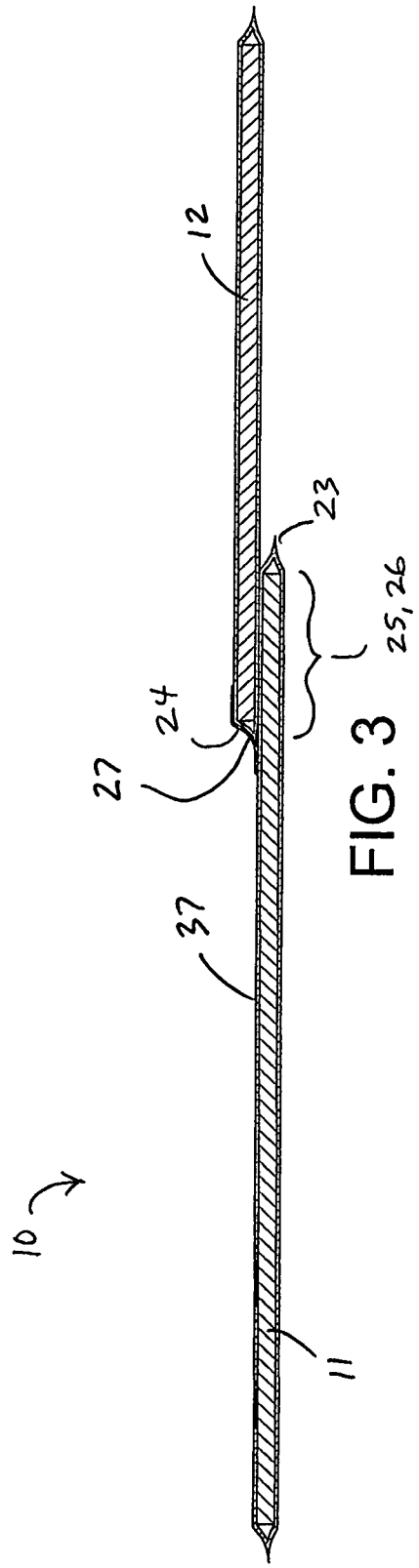
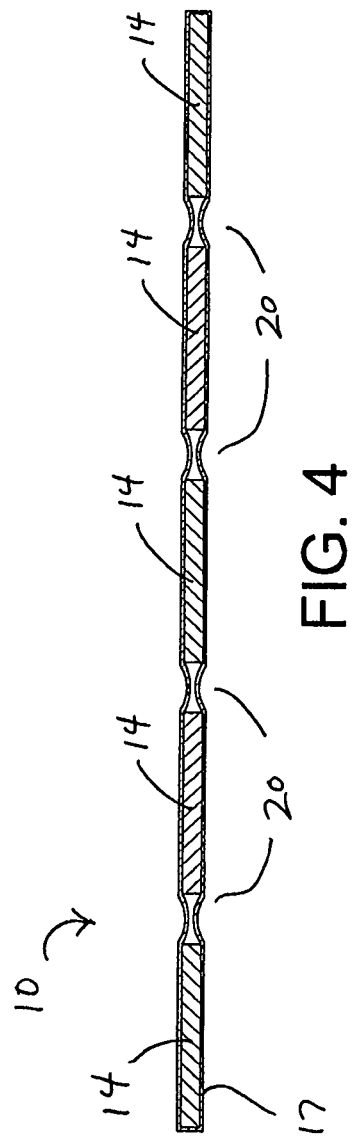

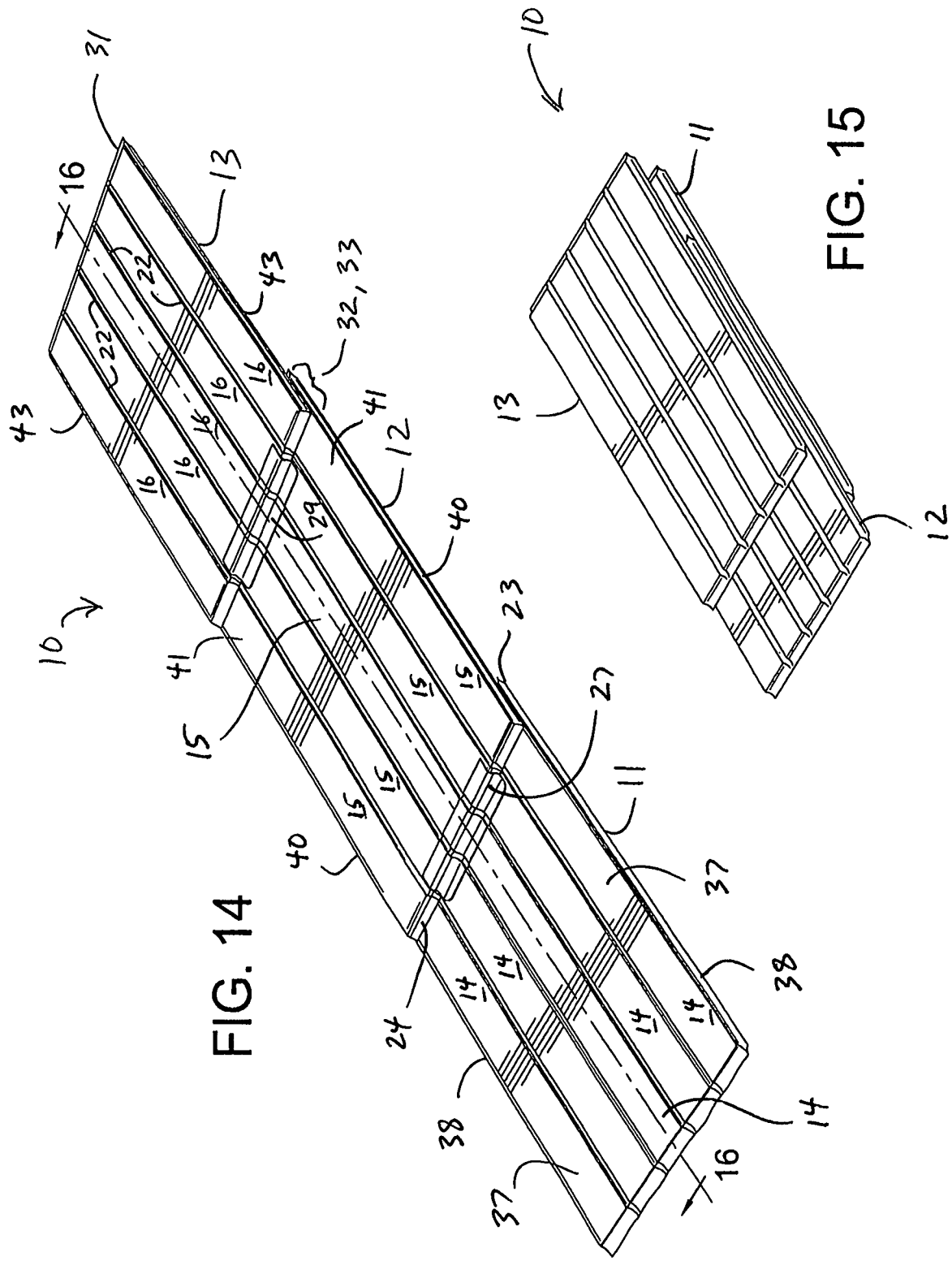

MEDICAL SPLINT

CROSS REFERENCE TO RELATED APPLICATIONS

The present application claims priority from provisional patent application No. 62/193,880, filed on Jul. 17, 2015. The present application also claims priority from nonprovisional patent application Ser. No. 15/212,283, filed on Jul. 17, 2016.

FIELD OF THE INVENTION

The subject invention relates generally to the field of first aid devices. The subject invention relates more specifically to emergency medical splints that can be quickly and easily applied to the limbs of a person.

BACKGROUND

A medical splint is used primarily as a short-term means for immobilizing a person's limb (arm, leg, etc.) following an injury. If the limb is not immobilized, then the injured person can experience excruciating pain caused by the unrestricted movement of bone ends and fragments in the limb, and the injured person can further injure soft tissues and blood vessels in the limb.

If an injury is minor, such as a slight joint sprain that only requires a relatively short treatment period, then the medical splint can serve as the primary means of treatment for the duration of the treatment period. If the injury is more severe, however, such as a broken bone or a torn ligament, then the medical splint usually serves as an immediate, temporary means of treatment until a more long-term means of treatment, such as a brace or cast, is available.

Regardless of whether a medical splint is used to provide primary or temporary treatment, effective immobilization of a person's limb is usually the goal. In most cases, medical splints are used under emergency conditions in locations remote from medical treatment facilities. Medical splints disclosed in the prior art are difficult to use in emergency situations; are cumbersome and awkward to carry and store in remote conditions; require assembly; can be easily damaged in storage; do not readily adapt to the contours of a human limb and require cutting of the medical splint to fit it to the injured person's limb.

There is a need for a compact, lightweight, portable, foldable, multi-purpose, multi-functional, medical splint, primarily to use in emergency and/or remote situations to effectively provide quick, easy, and rigid immobilization to a person's limbs. Such a medical splint should be compact, lightweight, portable, foldable, expandable, easy to carry, and easy to use. Such a medical splint should also be strong enough to restrain and support a person's limb until the person can receive medical attention in a proper medical facility. The medical splint of the present has been developed to satisfy those needs.

BRIEF DESCRIPTION OF THE DRAWINGS

The accompanying drawing is provided for the purpose of illustration only and is not intended as a definition of the limits of the present invention. The drawing illustrates a preferred embodiment of the present invention, wherein:

FIG. 1 is a perspective view of the medical splint.

FIG. 2 is a perspective view showing the medical splint in a folded position.

FIG. 3 is a cross-sectional view of the medical splint taken along line 3-3 of FIG. 1.

FIG. 4 is a cross-sectional view of the medical splint taken along line 4-4 of FIG. 1.

FIG. 14 is a perspective view of an alternative embodiment of the medical splint, having three sections instead of two sections.

FIG. 15 is a perspective view of an alternative embodiment of the medical splint, showing the alternative embodiment in a folded position.

DESCRIPTION OF THE INVENTION

Figure 5:
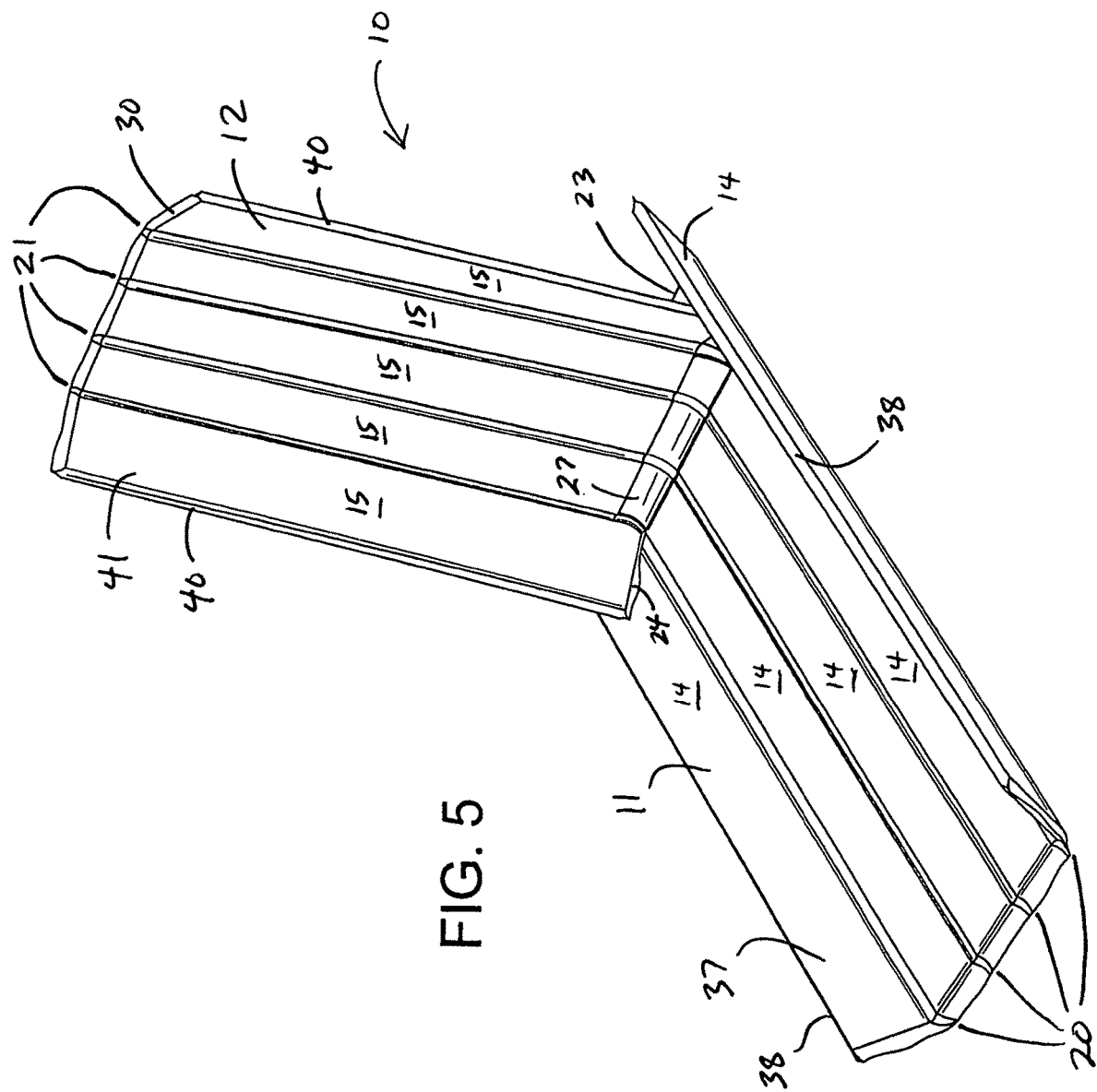
FIG. 5 is another perspective view of the medical splint, showing the two sections having an angle between one another.

While the present invention will be described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the present invention not be limited to the particular embodiments disclosed as the best mode contemplated for carrying out this invention, but that the invention will include all embodiments (and legal equivalents thereof).

Referring to the drawings, the present invention is a medical splint 10 used for securing an injured person's limbs (arms, legs, etc.). Medical splint 10 is designed to be used independently of other splints. Medical splint 10 does not need to be cut or assembled together to secure an injured person's body limb. Medical splint 10 does not need a kit to secure an injured person's body limb. All that is needed to secure medical splint 10 to an injured person's body limb is heavy duty tape/medical tape/bandaging. Medical splint 10 can be reused if decontaminated properly. Medical splint 10 can be easily stored without risk of breaking or deforming. Medical splint 10 can also be used as an IV board to immobilize an injured person's arm when applying an IV.

When used as an immobilization device, medical splint 10 reminds an injured person not to bend his or her arm while the IV is in place.

Referring to FIGS. 1 and 14, medical splint 10 consists of two or more elongated sections, designated as 11 and 12 in FIG. 1, and designated as 11, 12, and 13 in FIG. 14. First elongated section 11 is preferably approximately twelve inches long, six inches wide, and ⅛ inches thick. Second elongated section 12 is preferably approximately ten and one-half inches long, six inches wide, and ⅛ inches thick. Third elongated section 13 is preferably approximately nine inches long, six inches wide, and ⅛ inches thick.

As shown in FIGS. 1 and 14, each of first section 11, second section 12, and third section 13 of medical splint 10 preferably consists of a set of substantially rectangular slats 14, 15, and 16, arranged in a side-by-side, parallel configuration. The side-by-side, parallel configuration of slats 14, 15, and 16 allows elongated sections 11, 12, and 13 to conform to the limbs of an injured person, as discussed in more detail below. The conforming nature of elongated sections 11, 12, and 13 eliminates the need for adding bandages or dressing to fill voids when applying medical splint 10 to the limbs of an injured person.

Slats 14, 15, and 16 are preferably cut from a ⅛ inch thick sheet of material to produce slats 14, 15, and 16 having an elongated planar configuration of desired length and width, as discussed below. Slats 14, 15, and 16 are preferably substantially rigid to the extent that they exhibit only a limited degree of elasticity and deformability when subjected to manually applied forces. Materials satisfying these criteria at a thickness of about ⅛ of an inch include certain lightweight plastics and woods, but slats 14, 15, and 16 can be made with any material of suitable weight and rigidity, such as lightweight metals, although metals tend to interfere with X-rays and could hinder a medical professional treating a patient fitted with a medical splint 10 equipped with metal slats.

Slats 14 in first elongated section 11 are preferably approximately twelve inches long, one inch wide, and ⅛ inches thick. Slats 15 in second elongated section 12 are preferably approximately ten and one-half inches long, one inch wide, and ⅛ inches thick. Slats 16 in third elongated section 13 are preferably approximately nine inches long, one inch wide, and ⅛ inches thick.

Slats 14, 15, and 16 are preferably housed in a non-abrasive, inert material, which is designated as 17, 18, and 19, respectively. Housing material 17, 18, and 19 is preferably strong and flexible, but not substantially stretchable. Housing material 17, 18, and 19 is preferably impervious to moisture, dirt and most chemicals so that the material does not degrade over time. An example of a suitable material for housing material 17, 18, and 19 is nylon.

Referring to FIG. 14, housing materials 17, 18, and 19 preferably have linear, longitudinal fold lines 20, 21, and 22 between and parallel with slats 14, 15, and 16, respectively. Fold lines 20, 21, and 22 render housing materials 17, 18, and 19 more flexible and inelastically deformable at the position of fold lines 20, 21, and 22, and permit housing materials 17, 18, and 19 to be bent along fold lines 20, 21, and 22, as shown in FIGS. 5, 6, 8, 9, 10, 11, 12, and 13, thereby enabling sections 11, 12, and 13 of medical splint 10 to wrap into a U-shaped configuration around the outside of a person's injured limb, as shown in FIGS. 8, 9, 10, 11, and 12.

Figure 6:
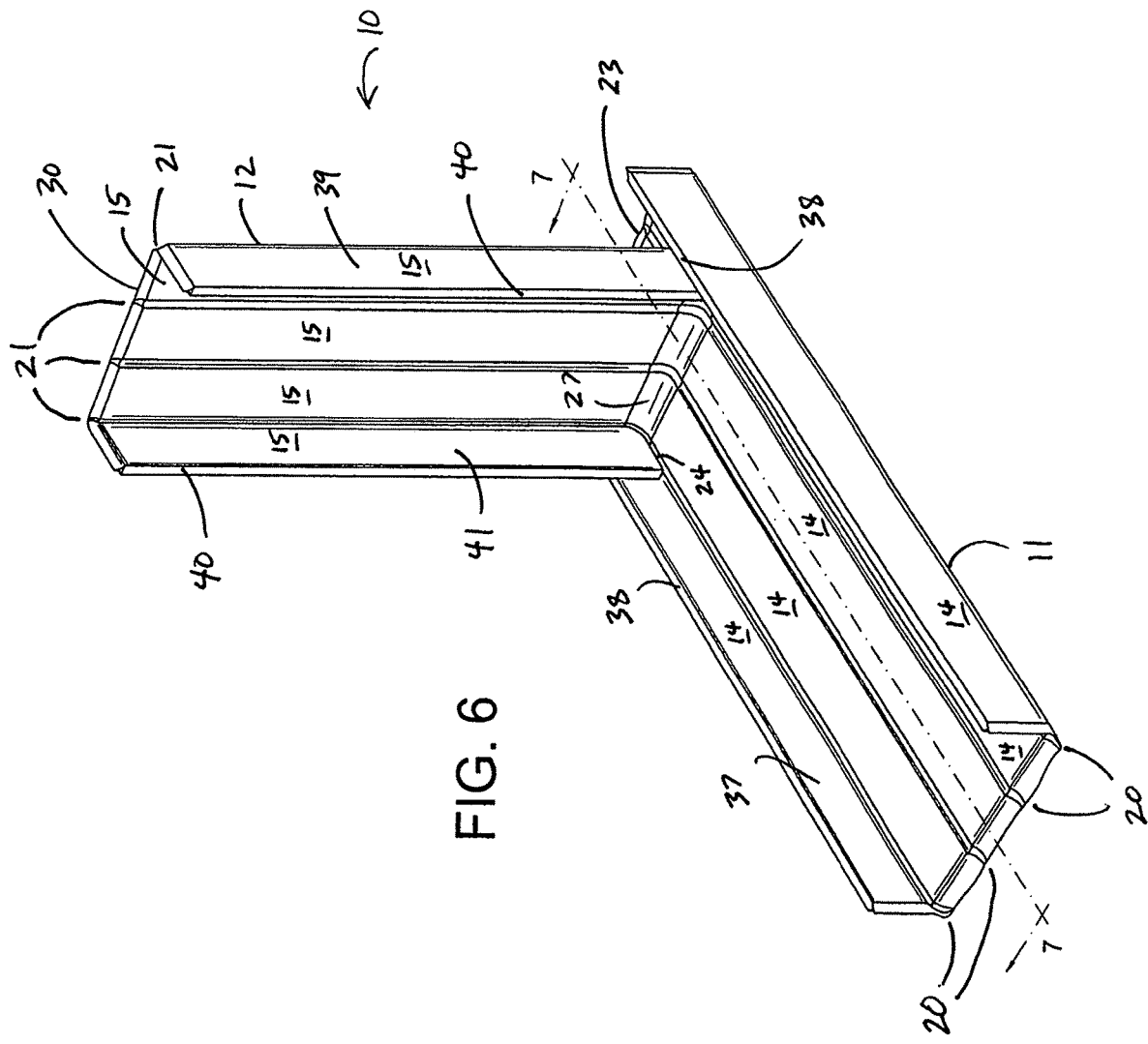
FIG. 6 is another perspective view of the medical splint, showing the two sections having a 90 degree angle between one another.
Figure 7:
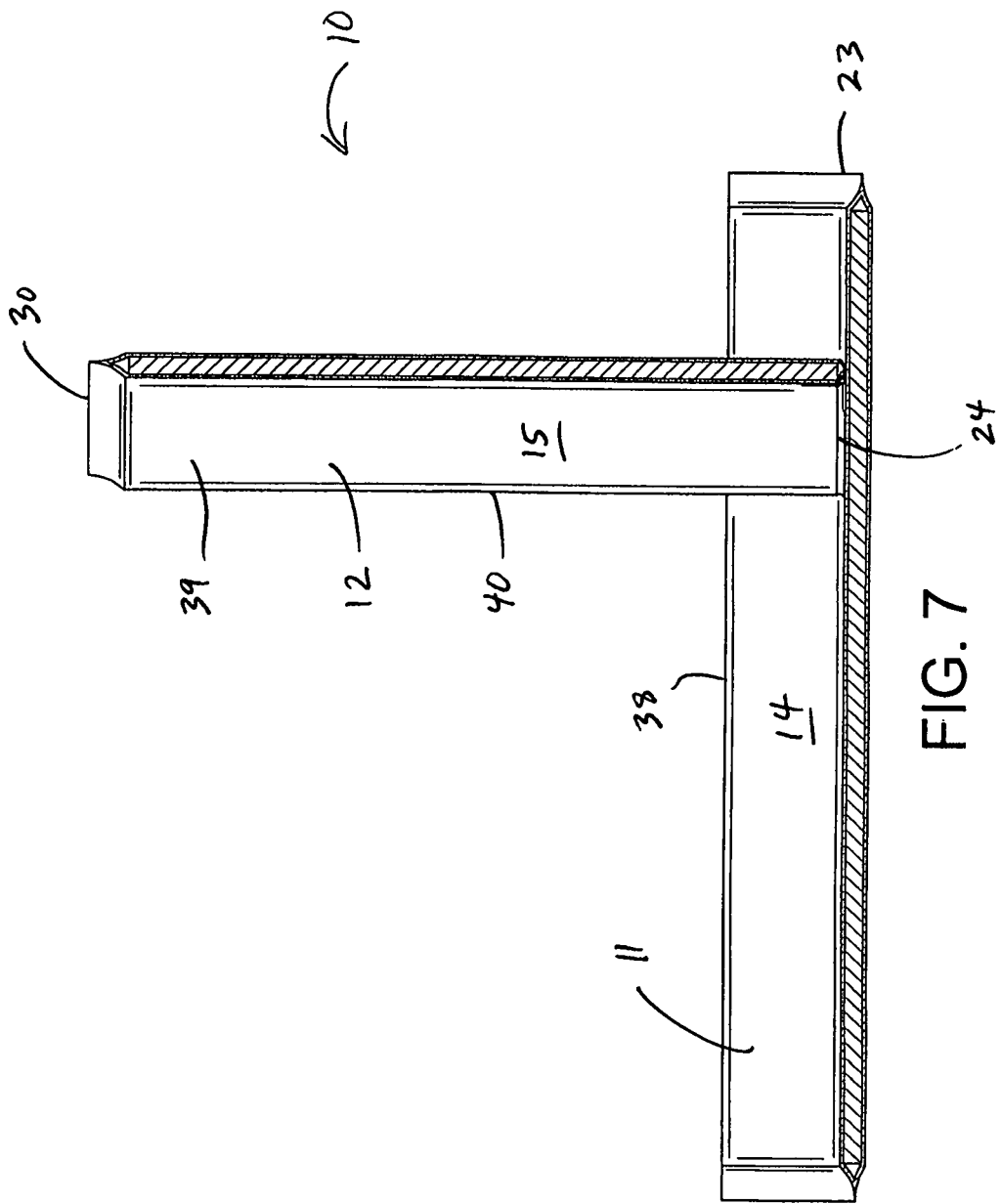
FIG. 7 is a cross-sectional view of the medical splint taken along line 7-7 of FIG. 6.
Figure 8:
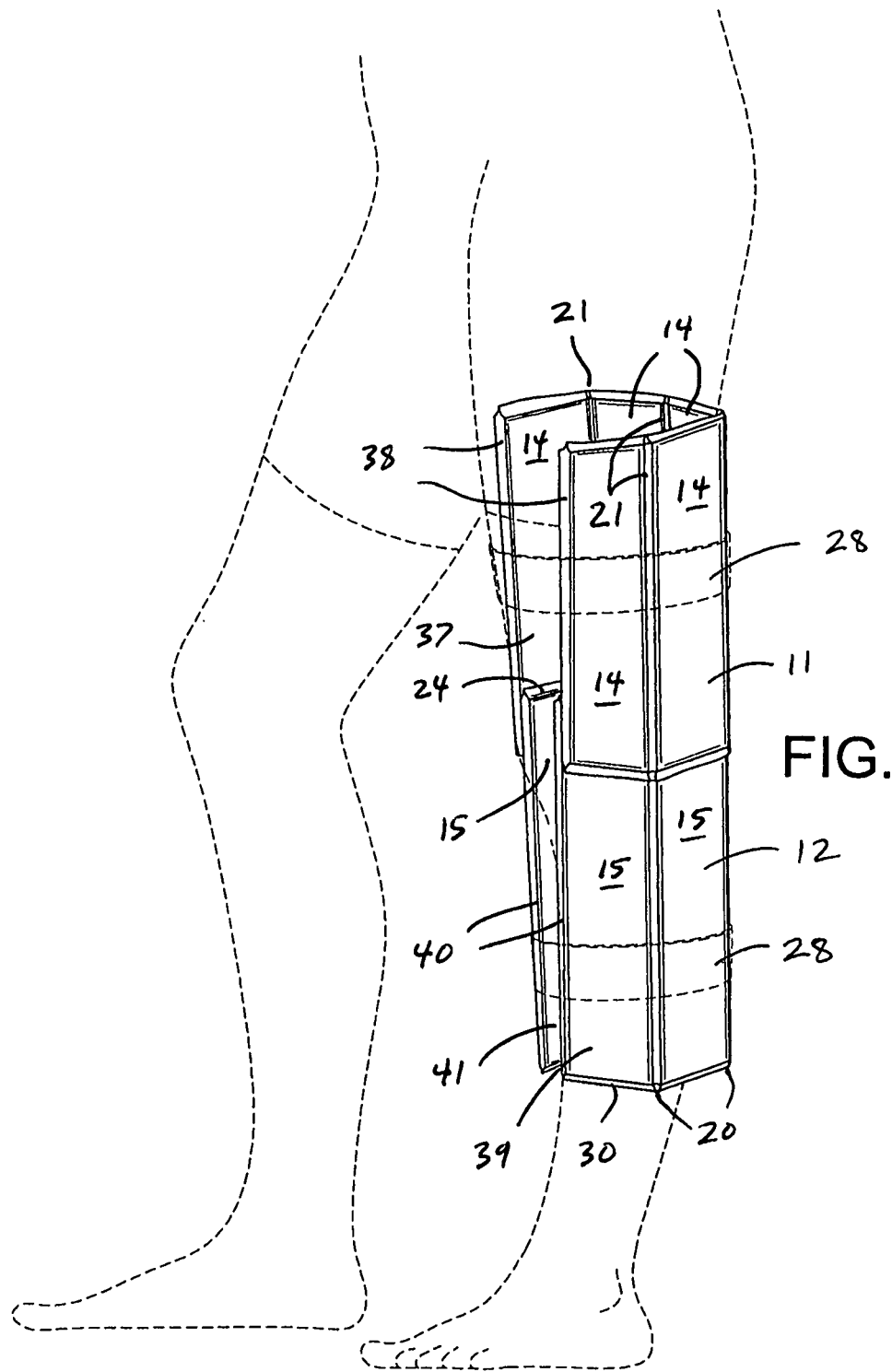
FIG. 8 is a perspective view of the medical splint attached to a person's leg.

As shown in FIGS. 1 and 3, first elongated section 11 has a pivotal connection 27 with second elongated section 12 at a point where first end 24 of second elongated section 12 overlaps end 23 of first elongated section 11. Pivotal connection 27 between first elongated section 11 and second elongated section 12 is in substantially perpendicular alignment with the longitudinal axis of first elongated section 11 and second elongated section 12. Pivotal connection 27 between first elongated section 11 and second elongated section 12 allows one-way angular articulation between the two sections, as shown in FIGS. 5, 6, 7, 9, 10, and 12, so that the range of angular articulation between the two sections is 0 degrees to 180 degrees. An angular articulation of 0 degrees between first elongated section 11 and second elongated section 12 results in second elongated section 12 being folded onto first elongated section 11, as shown in FIGS. 2, 11, and 13. An angular articulation of 180 degrees between first elongated section 11 and second elongated section 12 results in first elongated section 11 and second elongated section 12 lying in substantially the same plane, as shown in FIGS. 1, 3, and 8.

The overlap between first end 24 of second elongated section 12 and end 23 of first elongated section 11 prevents the angular articulation between the two sections to increase above 180 degrees. When the angular articulation between first elongated section 11 and second elongated section 12 is 180 degrees, as shown in FIGS. 1, 3, and 8, the portion 26 of second elongated section 12 between pivotal connection 27 and first end 24 lies against the portion 25 of first elongated section 11 between pivotal connection 27 and end 23, resulting in portion 25 providing rigid, linear support for second elongated section 12. The rigid, linear support permits first elongated section 11 and second elongated section 12 to act in unison like a stiff board and helps to prevent first elongated section 11 and second elongated section 12 from articulating beyond 180 degrees.

As shown in FIG. 1, pivotal connection 27 between first elongated section 11 and second elongated section 12 is limited to inners slats 14 and 15 near end 23 of first elongated section 11 and first end 24 of second elongated section 12, respectively. The limited width of pivotal connection 27 allows outer slats 14 of first elongated section 11 to pivot along the outer most fold lines 20 from a first position where outer slats 14 are horizontally aligned with a plane defined by inner slats 14, as shown in FIG. 1, to a second position where outer slats 14 form an angle with respect to the plane of inner slats 14, as shown in FIGS. 5, 6, 9, 10, 11, and 12. Likewise, the limited width of pivotal connection 27 allows outer slats 15 of second elongated section 12 to pivot along the outer most fold lines 21 from a first position where outer slats 15 are horizontally aligned with a plane defined by inner slats 15, as shown in FIG. 1, to a second position where outer slats 15 form an angle with respect to the plane of inner slats 15, as shown in FIGS. 5, 6, 9, 10, 11, and 12.

In the configurations shown in FIGS. 5, 6, 7, 9, 10, and 12, where outer slats 14 of first elongated section 11 pivot along the outer most fold lines 20 to form an angle with respect to the plane of inner slats 14, and outer slats 15 of second elongated section 12 pivot along the outer most fold lines 21 to form an angle with respect to the plane of inner slats 15, outer slats 15 of second elongated section 12 are preferably positioned inside of outer slats 14 so that outer slats 14 can provide additional support to outer slats 15.

In use, it will be appreciated that medical splint 10 may be transported in a flat configuration (FIGS. 2 and 15) to the scene of an accident, and there quickly and conveniently positioned into a suitable configuration for use in immobilizing an injured upper arm, elbow, forearm, wrist, lower leg or ankle.

As shown in FIGS. 8, 9, 10, 11, and 12, medical splint 10 can be used in a folded position (FIG. 11), in an angled position (FIGS. 9, 10, and 12), or in an extended position (FIG. 8). Medical splint 10 can remain in a folded position, as shown in FIGS. 2 and 15, which allows medical splint 10 to contour to an injured person's arm when splinting the wrist, as shown in FIG. 11, while at the same time remaining rigid. In this position, medical splint 10 can double as an IV board when giving the injured person an IV.

Figure 9:
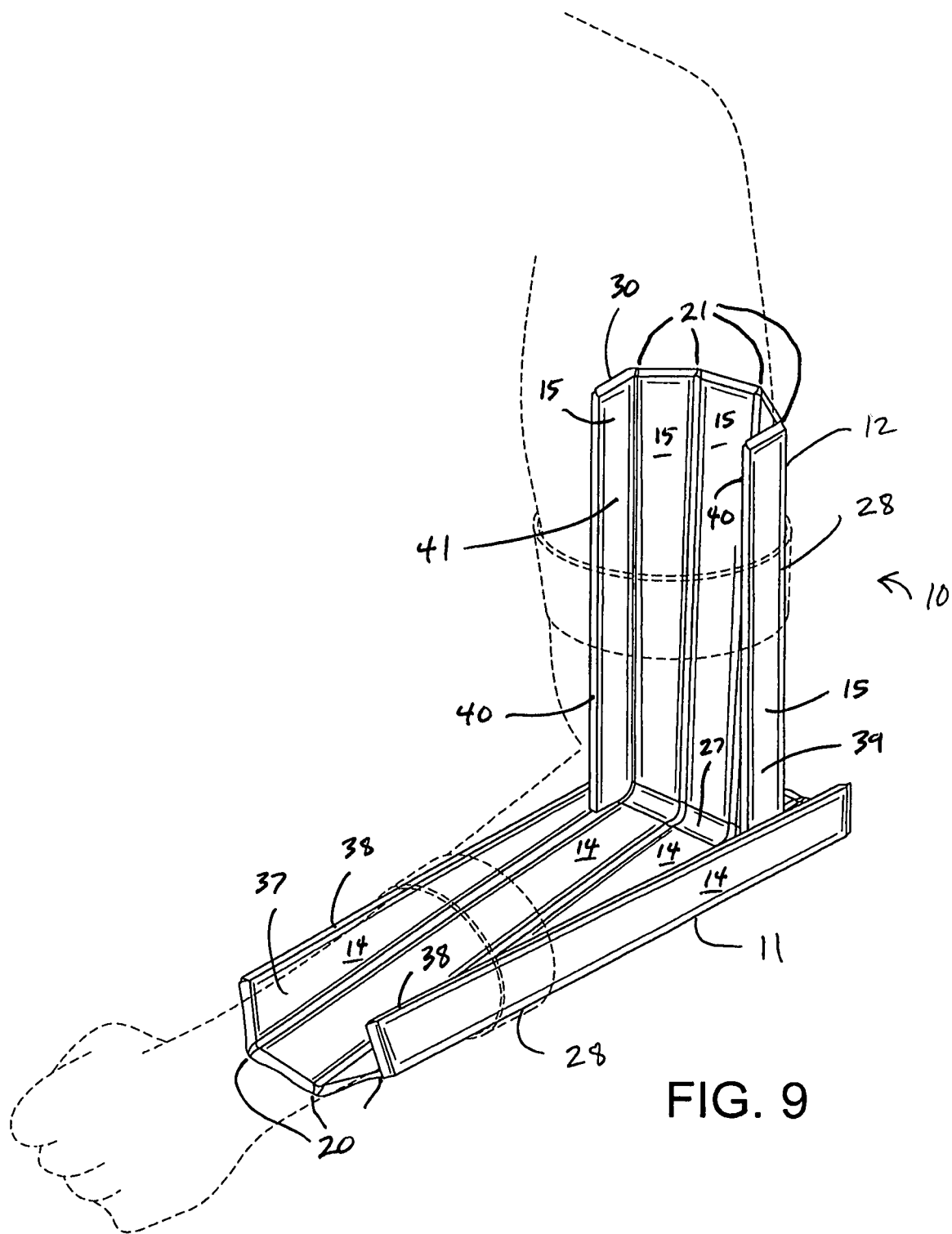
FIG. 9 is a perspective view of the medical splint attached to a person's arm.
Figure 10:
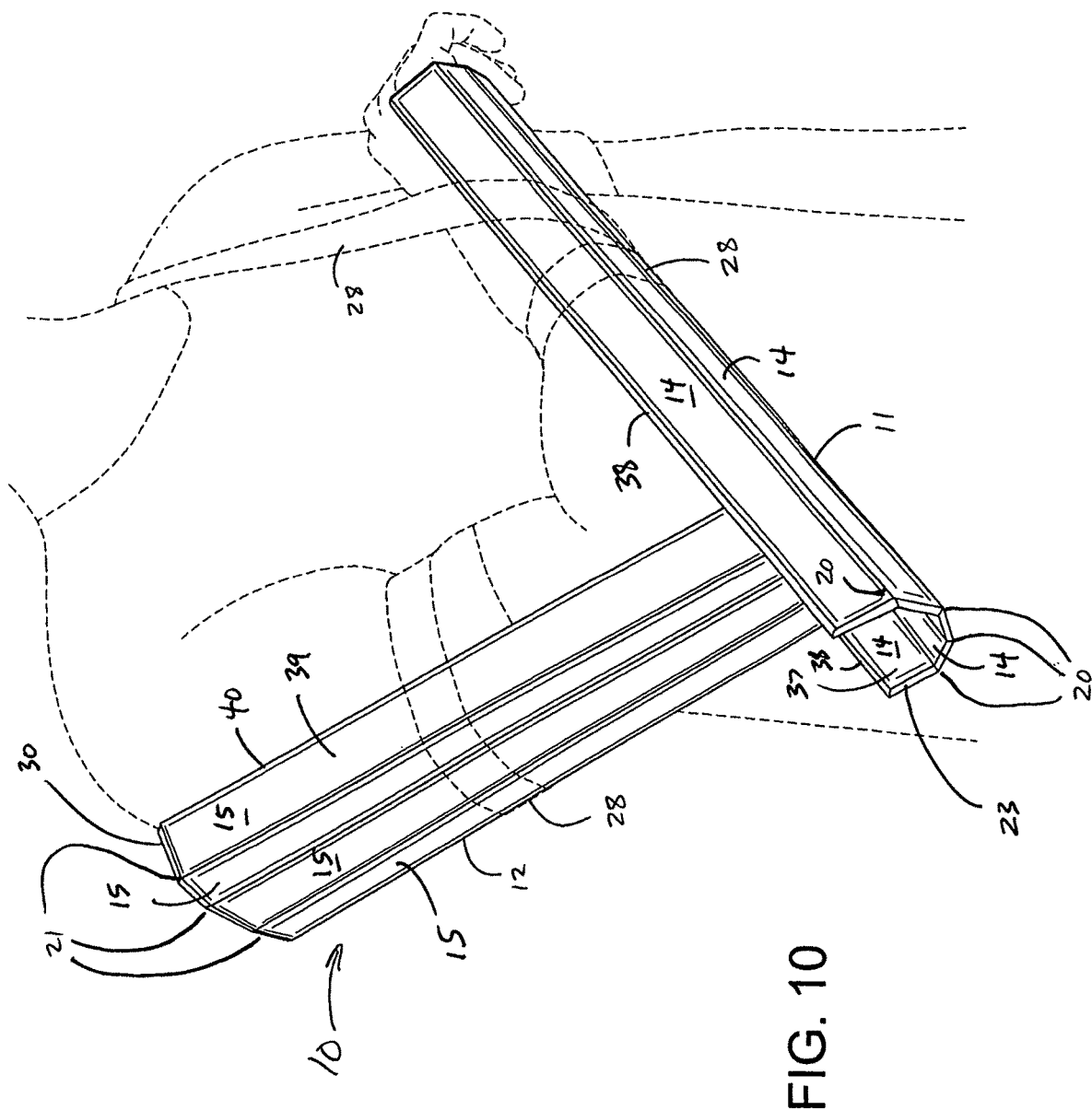
FIG. 10 is a perspective view of the medical splint attached to a person's arm.
Figure 11:
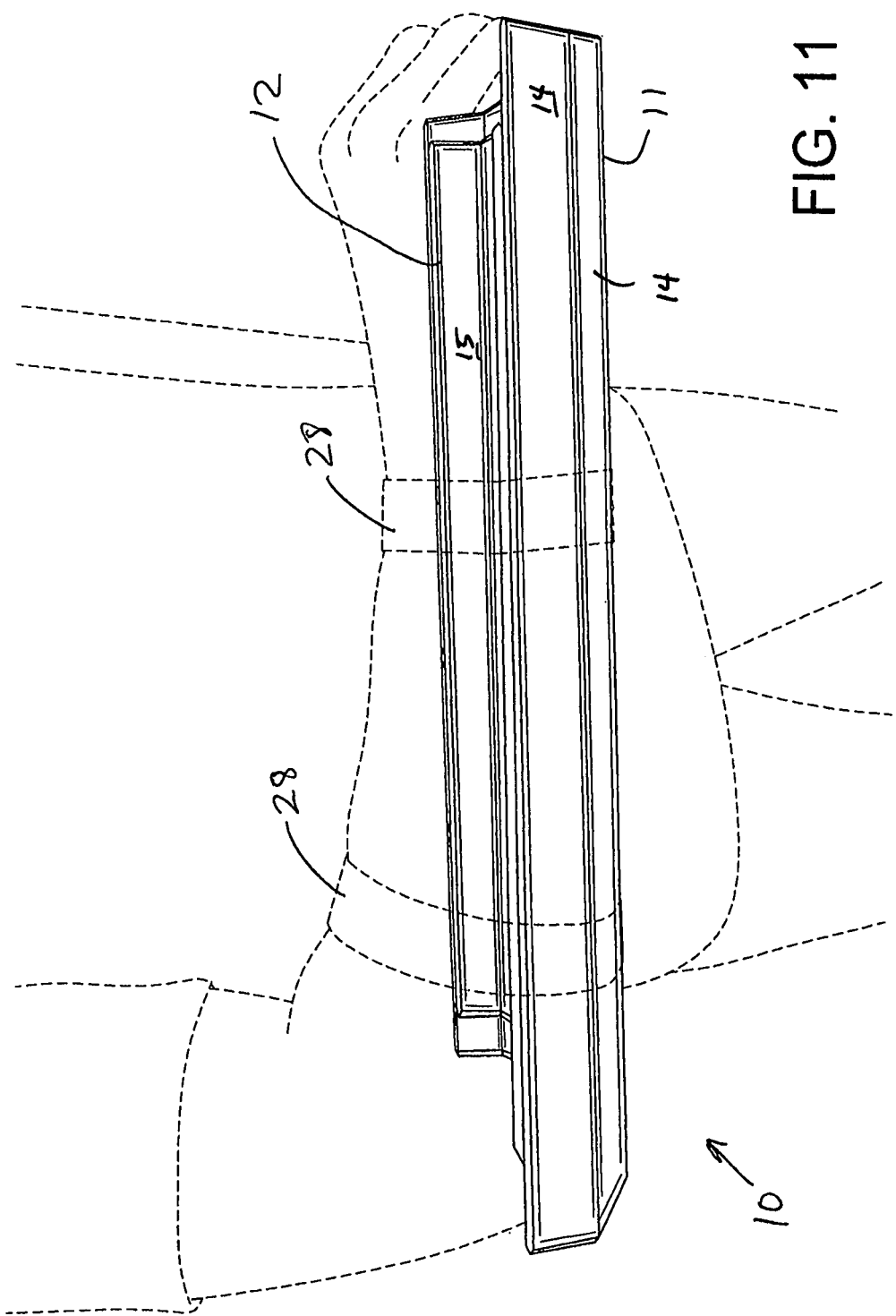
FIG. 11 is a perspective view of the medical splint attached to a person's arm.

When using medical splint 10 to secure the wrist, radial, ulna, elbow and clavicle, the injured person's arm is preferably in an "L-shape," as shown in FIGS. 5, 6, 7, 9, and 10. Splint 10 can quickly be folded into an "L-shape" without having to cut, tear, or assemble medical splint 10, and without having to place pieces of medical splint 10 into holes of any other part of medical splint 10. After positioning the injured person's arm in the shape of an "L," medical splint 10 can be snugly secured in the shape of an "L" to the injured person's arm using heavy duty tape/medical tape/bandaging 28, as shown in FIGS. 9, 10, and 11. Medical splint 10 and the injured person's arm can then be taped to the injured person's torso using heavy duty tape/medical tape/bandaging 28 to further secure the injured arm and to keep the injured arm close to injured person's body for protection, as shown in FIG. 10.

Figure 12:
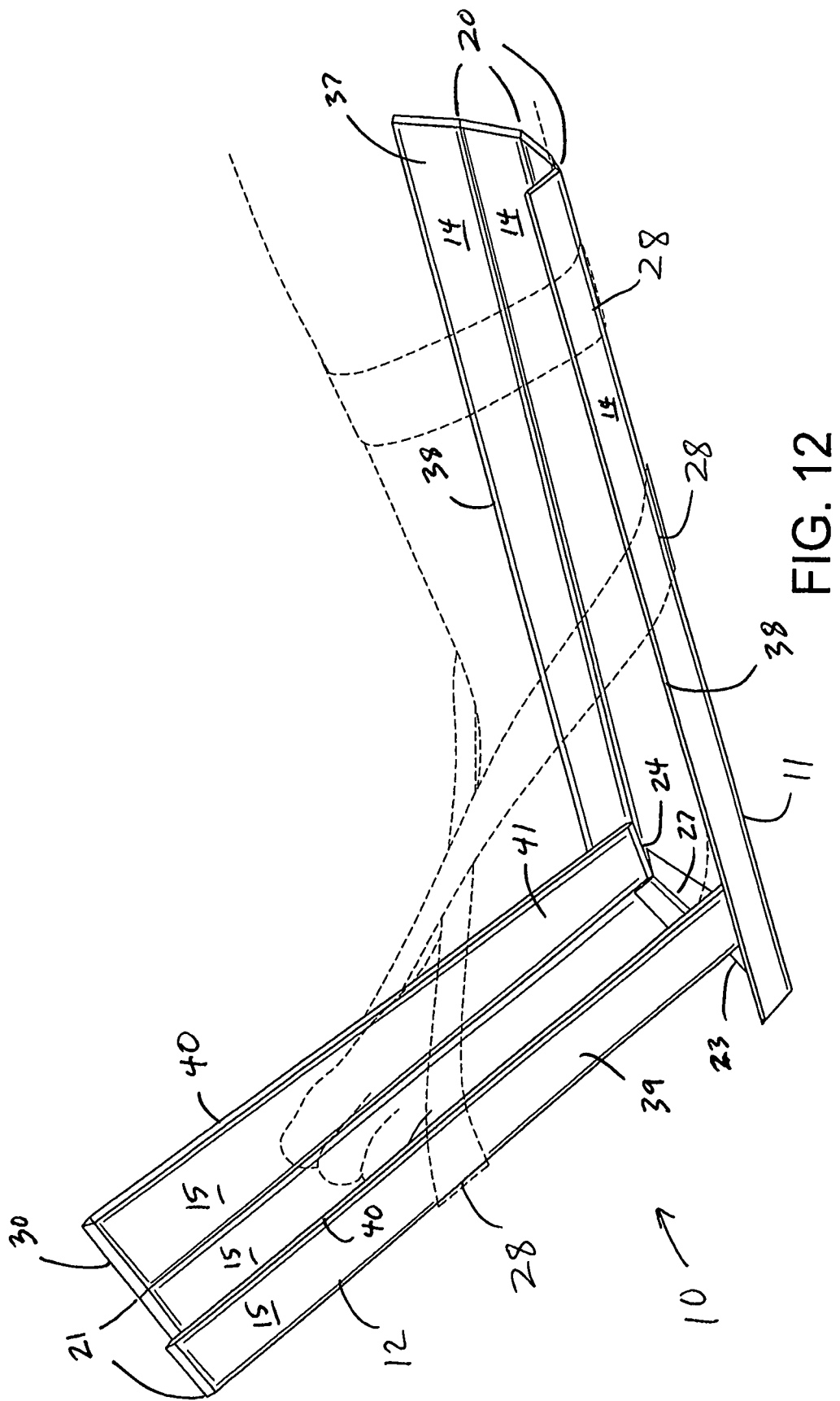
FIG. 12 is a perspective view of the medical splint attached to a person's lower leg and foot.
Figure 13:
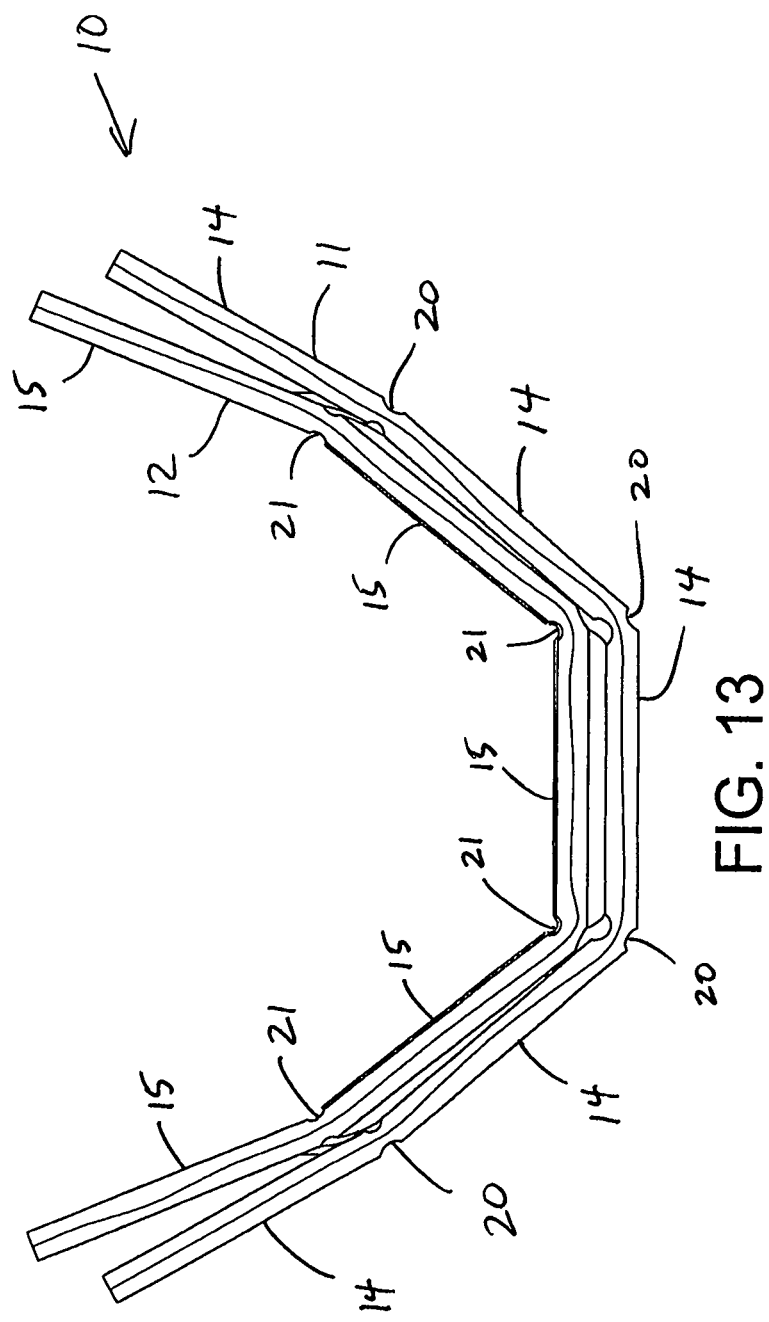
FIG. 13 is an end view of the medical splint in a folded position.

The "L-shaped" configuration discussed above can also be used to secure an injured person's ankle, as shown in FIG. 12. Heavy duty tape/medical tape/bandaging 28 is preferably used to secure medical splint 10 to the injured person's ankle and leg, and then the heavy duty tape/medical tape/bandaging 28 is applied in a simple figure "8" configuration to prevent any unwanted flexing of the "L-shaped" configuration, as shown in FIG. 12.

When securing an injured person's knee in a straight-leg position, medical splint 10 can be extended into a flat position, placed along the bottom of the leg, contoured to leg, and then taped onto the leg, as shown in FIG. 8.

As previously mention, medical splint 10 is preferably waterproof and can be penetrated by X-rays (as long as slats 14, 15, and 16 are not metal). Consequently, there is little need to change medical splint 10 from time to time under adverse weather conditions, and medical splint 10 need not be removed immediately upon arrival at a hospital because the patient can be promptly X-rayed without removing medical splint 10. When not in use, medical splint 10 is preferably stored in a folded, flattened position.

Figure 16:
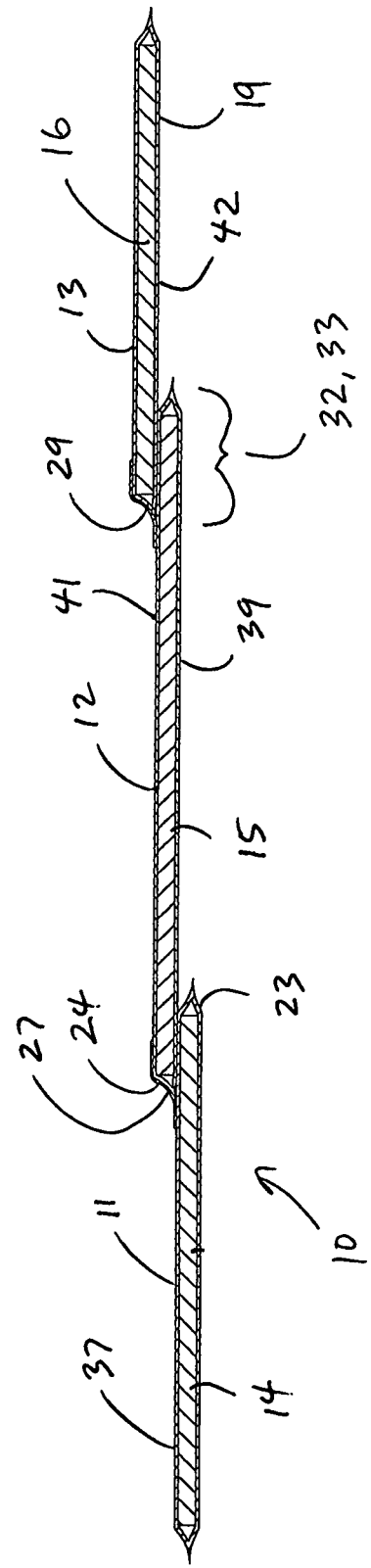
FIG. 16 is a cross-sectional view of an alternative embodiment of the medical splint, taken along line 16-16 of FIG. 14.
Figure 17:
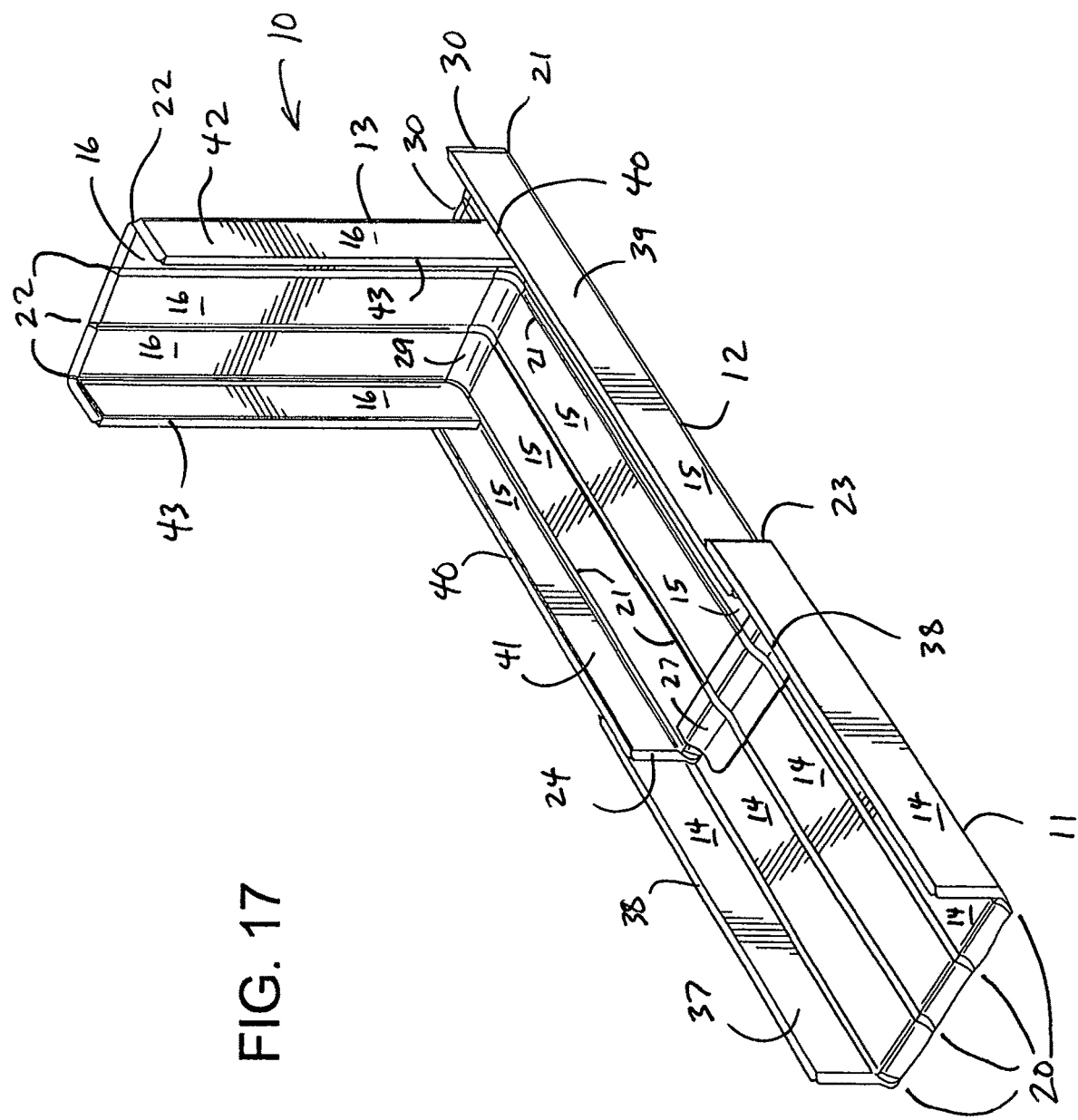
FIG. 17 is a perspective view of an alternative embodiment of the medical splint.

Various modifications may be made to medical splint 10. For example, if third elongated section 13 is included in medical splint 10, as shown in FIGS. 14 through 17, then third elongated section 13 is pivotally connected to second elongated section 12 at pivotal connection 29, which is preferably at a point where end 31 of third elongated section 13 overlaps second end 31 of second elongated section 12, as shown in FIGS. 14 and 16. Pivotal connection 29 between second elongated section 12 and third elongated section 13 is in substantially perpendicular alignment with the longitudinal axis of second elongated section 12 and third elongated section 13. Pivotal connection 29 between second elongated section 12 and third elongated section 13 allows one-way angular articulation between the two sections, as shown in FIG. 17, so that the range of angular articulation between the two sections is 0 degrees to 180 degrees. An angular articulation of 0 degrees between second elongated section 12 and third elongated section 13 results in third elongated section 13 being folded onto second elongated section 12, as shown in FIG. 15. An angular articulation of 180 degrees between second elongated section 12 and third elongated section 13 results in second elongated section 12 and third elongated section 13 lying in substantially the same plane, as shown in FIGS. 14 and 16.

The overlap between end 31 of third elongated section 13 and second end 30 of second elongated section 12 prevents the angular articulation between the two sections to increase above 180 degrees. When the angular articulation between second elongated section 12 and third elongated section 13 is 180 degrees, as shown in FIGS. 14 and 16, the portion 33 of third elongated section 13 between pivotal connection 29 and end 31 lies against the portion 32 of second elongated section 12 between pivotal connection 29 and second end 30, resulting in portion 32 providing rigid, linear support for third elongated section 13.

As shown in FIGS. 14 and 17, pivotal connection 29 between second elongated section 12 and third elongated section 13 is limited to inners slats 15 and 16. The limited width of pivotal connection 29 allows outer slats 15 of second elongated section 12 to pivot along the outer most fold lines 21 from a first position where outer slats 15 are horizontally aligned with a plane defined by inner slats 15, as shown in FIG. 14, to a second position where outer slats 15 form an angle with respect to the plane of inner slats 15, as shown in FIG. 17. Likewise, the limited width of pivotal connection 29 allows outer slats 16 of third elongated section 13 to pivot along the outer most fold lines 22 from a first position where outer slats 16 are horizontally aligned with a plane defined by inner slats 16, as shown in FIG. 14, to a second position where outer slats 16 form an angle with respect to the plane of inner slats 16, as shown in FIG. 17.

In the configuration shown in FIG. 17, where outer slats 15 of second elongated section 12 pivot along the outer most fold lines 21 to form an angle with respect to the plane of inner slats 15, and outer slats 16 of third elongated section 13 pivot along the outer most fold lines 22 to form an angle with respect to the plane of inner slats 16, outer slats 16 of third elongated section 13 are preferably positioned inside of outer slats 15 so that outer slats 15 can provide additional support to outer slats 16.

Figure 18:
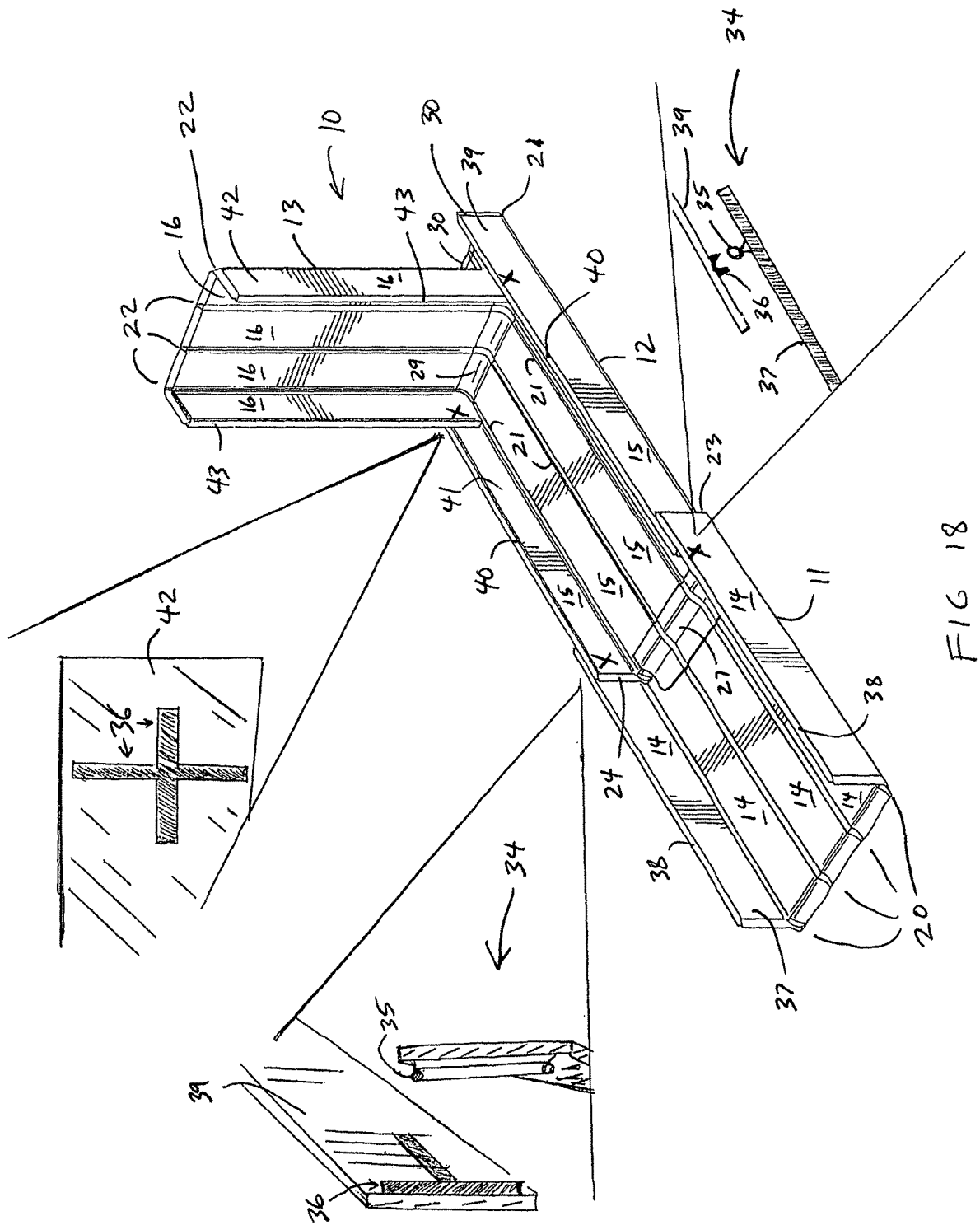
FIG. 18 is a perspective view of the medical splint showing locking mechanisms.

Additional support between first elongated section 11 and second elongated section 12 and between second elongated section 12 and third elongated section 13 can be provided by one or more locking mechanisms 34, shown in FIG. 18. Each locking mechanism 34 preferably has a male connector 35 and one or more female connectors 36. Male connector 35 is preferably designed to snap in and out of a female connector 36.

To provide additional support between first elongated section 11 and second elongated section 12, male connector 35 is preferably located on the upper surface 37 of first elongated section 11 on the outer most slats 14 adjacent to each side 38 of first elongated section 11 near end 23 of first elongated section 11. Female connector 36 is preferably located on the lower surface 39 of second elongated section 12 on the outer most slats 15 adjacent to each side 40 of second elongated section 12 near first end 24 of second elongated section 12. Female connector 36 can be located in more than one location to receive male connector 35 when the angle between first elongated section 11 and second elongated section 12 is zero degrees, as shown in FIGS. 17 and 18, and to receive male connector 35 when the angle between first elongated section 11 and second elongated section 12 is 90 degrees, as shown in FIGS. 6 and 7.

To provide additional support between second elongated section 12 and third elongated section 13, male connector 35 is preferably located on the upper surface 41 of second elongated section 12 on the outer most slats 15 adjacent to each side 40 of second elongated section 12 near second end 30 of second elongated section 12. Female connector 36 is preferably located on the lower surface 42 of third elongated section 13 on the outer most slats 16 adjacent to each side 43 of third elongated section 13 near end 31 of third elongated section 13. Female connector 36 can be located in more than one location to receive male connector 35 when the angle between second elongated section 12 and third elongated section 13 is zero degrees, and to receive male connector 35 when the angle between second elongated section 12 and third elongated section 13 is 90 degrees, as shown in FIGS. 17 and 18.

Male connector 35 and female connector 36 will make medical splint 10 more user friendly and faster to apply. Male connector 35 and female connector 36 will allow medical splint 10 to be locked into position at either zero degrees or 90 degrees between adjacent elongated sections so that the user does not need to hold medical splint 10 in that position when securing medical splint 10 to the patient.

It is understood that one or more embodiments of the present invention have been disclosed by way of example and that other modifications and alterations may occur to those skilled in the art without departing from the scope and spirit of the present invention.

What is claimed is:

1. A medical splint comprising:
   (a) a first elongated section having a first end, a second end, an upper surface, and two sides, said first elongated section comprising a set of inner slats arranged in a substantially side-by-side, parallel configuration, and at least one outer slat on each side of said set of inner slats, where said at least one outer slat are arranged in a substantially side-by-side, parallel configuration with said set of inner slats, where said set of inner slats and said at least one outer slat in said first elongated section are housed in a material, said material having fold lines between and parallel to said inner slats and said at least one outer slat in said first elongated section;
   (b) a second elongated section having a first end, a second end, a lower surface, and two sides, said second elongated section comprising a set of inner slats arranged in a substantially side-by-side, parallel configuration, and at least one outer slat on each side of said set of inner slats, where said at least one outer slat are arranged in a substantially side-by-side, parallel configuration with said set of inner slats, where said inner slats and said at least one outer slat in said second elongated section are housed in a material, said material having fold lines between and parallel to said inner slats and said at least one outer slat in said second elongated section, said set of inner slats of said second elongated section having a pivotal connection with said set of inner slats of said first elongated section near said second end of said first elongated section and near said first end of said second elongated section, where said pivotal connection between said set of inner slats of said first elongated section and said set of inner slats of said second elongated section allows angular articulation between said first elongated section and said second elongated section;
   (c) locking mechanisms for maintaining a desired angle between said first elongated section and said second elongated section, each locking mechanism having a male connector and at least one female connector, where said male connector is designed to snap in and out of said at least one female connector, where said male connector is located on said upper surface of said first elongated section on said at least one outer slat of said first elongated section adjacent to each said side of said first elongated section near said second end of said first elongated section, and where said female connector is located on said lower surface of said second elongated section on said at least one outer slat of said second elongated section adjacent to each said side of said second elongated section near said first end of said second elongated section;
   (d) where a portion of said first elongated section between:
      (1) said second end of said first elongated section and;
      (2) said pivotal connection between said inner slats of said first elongated section and said inner slats of said second elongated section,
      provides linear support for said second elongated section when said angular articulation between said first elongated section and said second elongated section is 180 degrees; and
   (e) where said female connector is located to receive said male connector when said angular articulation between said first elongated section and said second elongated section is zero degrees.

2. The medical splint of claim 1, where said female connector is located to receive said male connector when said angular articulation between said first elongated section and said second elongated section is ninety degrees.

3. The medical splint of claim 2, where said set of inner slats and said at least one outer slat of said first elongated section comprises three inner slats and two outer slats.

4. The medical splint of claim 3, where said female connector on said second elongated section is located to receive said male connector on said first elongated section when said angular articulation between said first elongated section and said second elongated section is ninety degrees.

5. The medical splint of claim 4, where said set of inner slats and said at least one outer slat of said second elongated section comprises three inner slats and two outer slats.

6. The medical splint of claim 1, where said set of elongated inner slats and said at least one outer slat slats of said first and second elongated sections are made from a rigid material that exhibits only a limited degree of elasticity and deformability.

7. The medical splint of claim 6, where said set of inner slats and said at least one outer slat of said second elongated section comprises three inner slats and two outer slats.

8. The medical splint of claim 7, where said female connector on said third elongated section is located to receive said male connector on said second elongated section when said angular articulation between said second elongated section and said third elongated section is zero degrees.

9. The medical splint of claim 8, where said set of inner slats and said at least one outer slat of said third elongated section comprises three inner slats and two outer slats.

10. The medical splint of claim 1, where said material housing said set of elongated inner slats and said at least one outer slat of said first and second elongated sections is made from a non-abrasive, inert material.

11. A medical splint comprising:
   (a) a first elongated section having a first end, a second end, an upper surface, and two sides, said first elongated section comprising a set of inner slats arranged in a substantially side-by-side, parallel configuration, and at least one outer slat on each side of said set of inner slats, where said at least one outer slat are arranged in a substantially side-by-side, parallel configuration with said set of inner slats, where said inner slats and said at least one outer slat in said first elongated section are housed in a material, said material having fold lines between and parallel to said inner slats and said at least one outer slat in said first elongated section;

(b) a second elongated section having a first end, a second end, an upper surface, a lower surface, and two sides, said second elongated section comprising a set of inner slats arranged in a substantially side-by-side, parallel configuration, and at least one outer slat on each side of said set of inner slats, where said at least one outer slat are arranged in a substantially side-by-side, parallel configuration with said set of inner slats, where said inner slats and said at least one outer slat in said second elongated section are housed in a material, said material having fold lines between and parallel to said inner slats and said at least one outer slat in said second elongated section, said set of inner slats of said second elongated section having a pivotal connection with said set of inner slats of said first elongated section near said second end of said first elongated section and near said first end of said second elongated section, where said pivotal connection between said set of inner slats of said first elongated section and said set of inner slats of said second elongated section allows angular articulation between said first elongated section and said second elongated section;

(c) locking mechanisms for maintaining a desired angle between said first elongated section and said second elongated section, each locking mechanism having a male connector and at least one female connector, where said male connector is designed to snap in and out of said at least one female connector, where said male connector is located on said upper surface of said first elongated section on said outer slats of said first elongated section adjacent to each said side of said first elongated section near said second end of said first elongated section, and where said female connector is located on said lower surface of said second elongated section on said at least one outer slat of said second elongated section adjacent to each said side of said second elongated section near said first end of said second elongated section;

(d) a third elongated section having a first end, a second end, a lower surface, and two sides, said third elongated section comprising a set of inner slats arranged in a substantially side-by-side, parallel configuration, and at least one outer slat on each side of said set of inner slats, where said at least one outer slat data are arranged in a substantially side-by-side, parallel configuration with said set of inner slats, where said inner slats and said at least one outer slat in said third elongated section are housed in a material, said material having fold lines between and parallel to said inner slats and said at least one outer slat in said third elongated section, said set of inner slats of said third elongated section having a pivotal connection with said set of inner slats of said second elongated section near said second end of said second elongated section and near said first end of said third elongated section, where said pivotal connection between said set of inner slats of said second elongated section and said set of inner slats of said third elongated section allows one-way angular articulation between said second elongated section and said third elongated section;

(e) locking mechanisms for maintaining a desired angle between said second elongated section and said third elongated section, each locking mechanism having a male connector and at least one female connector, where said male connector is designed to snap in and out of said at least one female connector, where said male connector is located on said upper surface of said second elongated section on outer slats of said second elongated section adjacent to each said side of said second elongated section near said second end of said second elongated section, and where said female connector is located on said lower surface of said third elongated section on said at least one outer slat of said third elongated section adjacent to each said side of said third elongated section near said first end of said third elongated section;

(f) where a portion of said first elongated section between:
  (1) said second end of said first elongated section and;
  (2) said pivotal connection between said inner slats of said first elongated section and said inner slats of said second elongated section,
  provides linear support for said second elongated section when said angular articulation between said first elongated section and said second elongated section is 180 degrees; and (g) where a portion of said second elongated section between:
  (1) said second end of said second elongated section and;
  (2) said pivotal connection between said inner slats of said second elongated section and said inner slats of said third elongated section,
  provides linear support for said third elongated section when said angular articulation between said second elongated section and said third elongated section is 180 degrees; and (h) where said female connector on said second elongated section is located to receive said male connector on said first elongated section when said angular articulation between said first elongated section and said second elongated section is zero degrees.

12. The medical splint of claim 11, where said female connector on said third elongated section is located to receive said male connector on said second elongated section when said angular articulation between said second elongated section and said third elongated section is ninety degrees.

13. The medical splint of claim 11, where said set of inner slats and said at least one outer slat of said first, second, and third elongated sections are made from a rigid material that exhibits only a limited degree of elasticity and deformability.

14. The medical splint of claim 11, where said material housing said set of inner slats and said at least one outer slat of said first, second, and third elongated sections is made from a non-abrasive, inert material.

15. The medical splint of claim 11, where said set of inner slats and said at least one outer slat of said first elongated section comprises three inner slats and two outer slats.

* * * * *